US008580744B2

(12) United States Patent
Shanahan-Prendergast

(10) Patent No.: US 8,580,744 B2
(45) Date of Patent: Nov. 12, 2013

(54) THERAPEUTIC FORMULATIONS CONTAINING VENOM OR VENOM ANTI-SERUM EITHER ALONE OR IN COMBINATION FOR THE THERAPEUTIC PROPHYLAXIS AND THERAPY OF NEOPLASMS

(76) Inventor: Elizabeth Shanahan-Prendergast, Straffan (IE)

( * ) Notice: Subject to any disclaimer, the term of this patent is extended or adjusted under 35 U.S.C. 154(b) by 0 days.

(21) Appl. No.: 13/444,416

(22) Filed: Apr. 11, 2012

(65) Prior Publication Data

US 2012/0258115 A1 Oct. 11, 2012

Related U.S. Application Data

(63) Continuation of application No. 12/623,984, filed on Nov. 23, 2009, now abandoned, which is a continuation of application No. 11/735,025, filed on Apr. 13, 2007, now abandoned, which is a continuation of application No. 10/742,726, filed on Dec. 19, 2003, now abandoned, which is a continuation of application No. 09/254,623, filed as application No. PCT/IB97/01091 on Sep. 10, 1997, now abandoned.

(60) Provisional application No. 60/025,179, filed on Sep. 11, 1996.

(51) Int. Cl.
*A61K 39/395* (2006.01)

(52) U.S. Cl.
USPC ...................................... 514/19.2; 424/130.1

(58) Field of Classification Search
None
See application file for complete search history.

(56) References Cited

U.S. PATENT DOCUMENTS

| | | | |
|---|---|---|---|
| 4,822,608 A * | 4/1989 | Benton et al. | 424/539 |
| 5,019,508 A * | 5/1991 | Johnson et al. | 435/198 |
| 5,053,492 A * | 10/1991 | Rael et al. | 530/391.1 |
| 5,164,196 A | 11/1992 | Plata et al. | |
| 5,178,864 A | 1/1993 | Lees et al. | |
| 5,322,776 A | 6/1994 | Knopf et al. | |
| 5,565,431 A | 10/1996 | Lipps et al. | |
| 5,698,583 A | 12/1997 | Crescenti | |

FOREIGN PATENT DOCUMENTS

| | | |
|---|---|---|
| DE | 41 42 552 | 6/1993 |
| EP | 0 007 277 | 1/1980 |
| EP | 0 064 366 | 11/1982 |
| EP | 0 246 861 | 11/1987 |
| EP | 0 322 262 | 6/1989 |
| EP | 0 618 815 | 10/1994 |
| EP | 0 459 450 | 11/1995 |
| FR | 2 722 692 | 1/1996 |
| WO | 93/12816 A | 7/1993 |

OTHER PUBLICATIONS

Herbert et al., The dictionary of Immunol AP, 1995, 4$^{th}$ ed., p. 58.
Greenspan et al., Nature Biotech,1999, vol. 17 pp. 936-937.
Murakami, M Advances Experimental Medicine and Biology, 1992, 318:27-34.
Vera C.B. Cainelli Gebara, Vera L. Petricevich, Isaias Raw and Wilmar D. da Silva, "Effect of saponin from *Quillaja saponaria* (molina) on antibody tumour necrosis factor and interferon-γ production", Biotechnol. Appl. Biochem. 21, pp. 31-37 (1995).
Stedman's medical dictionary, 25$^{th}$ ed., 1990, pp. 1029-1030.
Chaim-Matyas et al., 1991, Biochem Intl. 24(e): 415-21.
Homma et al., "Growth Inhibition by Phospholipase C Inhibitor Peptides of Colorectal Carcinoma Cells Derived from Familial Adenomatous Polyposis", *Cell Growth & Differentiation*, vol. 7, Mar. 1996, pp. 281-288.
Tokumoto et al., "Phospholipase A$_2$-induced stimulation of A549 lung adenocarcinoma cell line proliferation", *Biochimica et Biophysica Acta*, 1164 (1993), BBALIP:54236, pp. 236-242.
Goldberg et al., 1993, Clin Chem, 39 (11 pt2): 2360-74.
Smith, B.D., 2001, Annals Otology, Rhinology, and Laryngology, 110 (3): 221-8.
Bertolini et al., 2000, Leukemia, 14: 1477-1482.
Essell (J. NIH Res. 1995 7:46).
Spitler (Cancer Biotherapy, 1995, 1 0:1-3).
Boon (Adv. Can. Res. 1992 58:177-210).
Hodgson et al, Clinical and Experimental Pharmacology and Physiology vol. 29 p. 807 (2002).
Chwetzoff et al, JBC vol. 164 p. 13289 (1989).
Sheu et al Jpn. J. Cancer Res. vol. 83 p. 885 (1992).
Chaim-Matyas et al Biochemistry International vol. 24 p. 415 (1991 ).

* cited by examiner

*Primary Examiner* — Sheela J Huff
(74) *Attorney, Agent, or Firm* — Burr & Brown

(57) ABSTRACT

A method of treating a mammal prophylactically to prevent neoplastic development comprises administering to the mammal a therapeutic vaccine comprising venom and at least one adjuvant. The method optionally further comprises administering to the mammal at least one other therapeutically effective agent, e.g., an anti-inflammatory agent.

16 Claims, 9 Drawing Sheets

Figure 1:
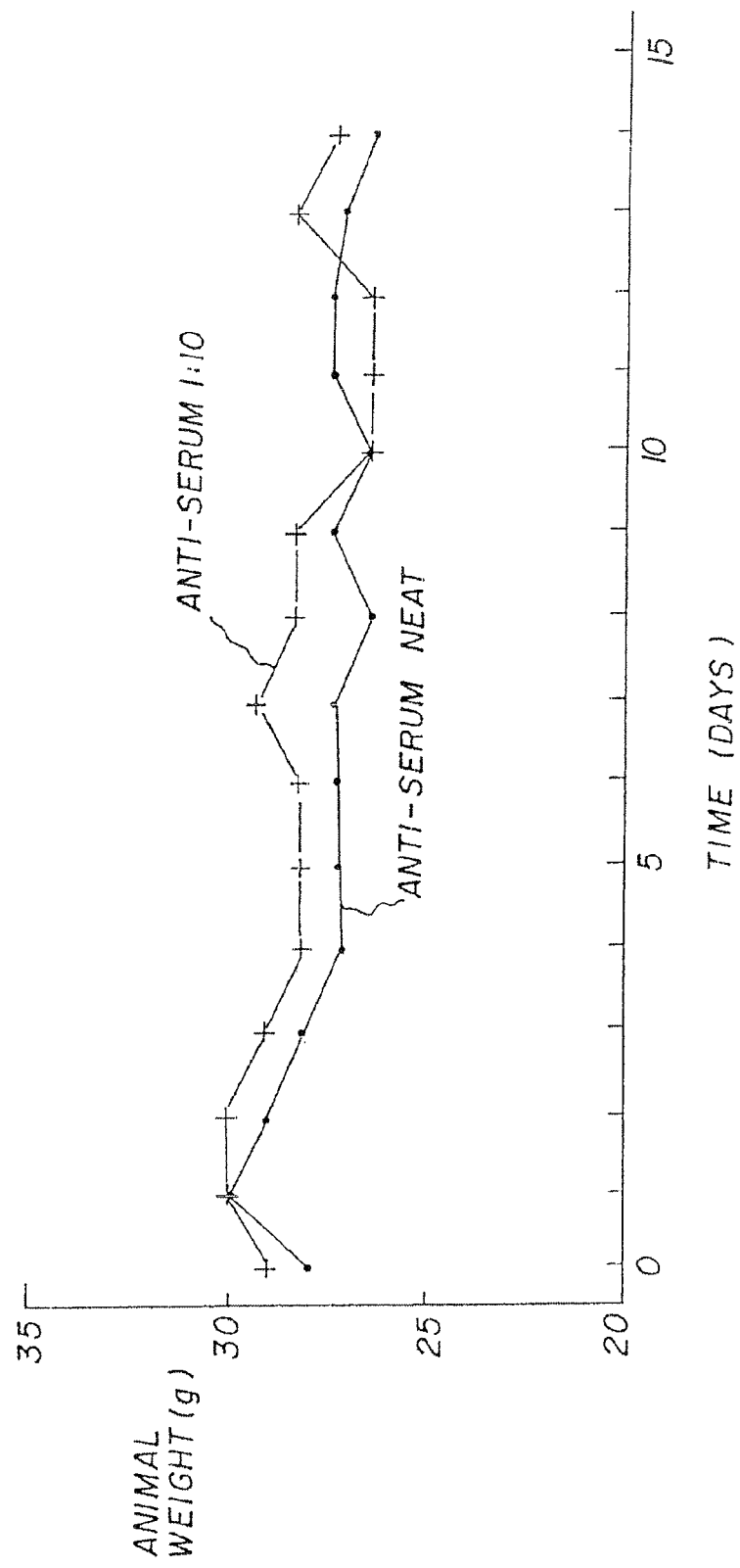

*Days are measured with day zero taken as day 7 past tumour inoculation.

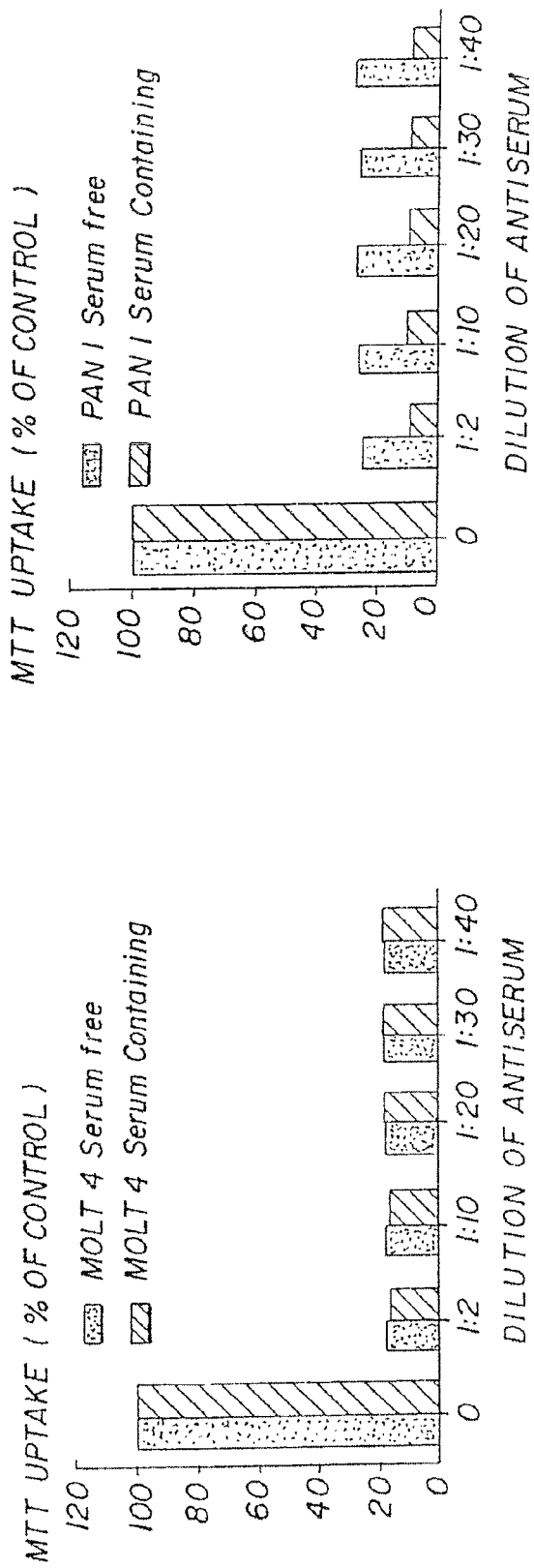

THERAPEUTIC FORMULATIONS CONTAINING VENOM OR VENOM ANTI-SERUM EITHER ALONE OR IN COMBINATION FOR THE THERAPEUTIC PROPHYLAXIS AND THERAPY OF NEOPLASMS

CROSS-REFERENCE TO RELATED APPLICATIONS

This application is a continuation of U.S. application Ser. No. 12/623,984 filed Nov. 23, 2009 (now abandoned) (the entirety of which is incorporated herein by reference), which is a continuation of U.S. application Ser. No. 11/735,025 filed Apr. 13, 2007 (now abandoned) (the entirety of which is incorporated herein by reference), which is a continuation of U.S. application Ser. No. 10/742,726 filed Dec. 19, 2003 (now abandoned) (the entirety of which is incorporated herein by reference), which is a continuation of U.S. application Ser. No. 09/254,623, filed Jul. 8, 1999 (now abandoned) (the entirety of which is incorporated herein by reference), which is the National Stage of PCT Application No. PCT/IB97/01091 filed Sep. 10, 1997 (now abandoned) (which designated the U.S.) (the entirety of which is incorporated herein by reference), which claims the benefit of U.S. Provisional Application Ser. No. 60/025,179 filed Sep. 11, 1996 (now abandoned) (the entirety of which is incorporated herein by reference).

The present invention comprises the method of treating a host organism (man or animal) in need of a drug having direct or prophylactic anti-neoplastic activity comprising the administration of a therapeutically effective amount of Phospholipase $A_2$ targeted venom anti-serum alone or in combination with a known Phospholipase C anti-serum or a Phospholipase C inhibitory compound. A vaccine containing in whole or in part snake or insect venom or mammalian $PLA_2$ components comprising epitopes demonstrating Phospholipase $A_2$ activity and/or Phospholipase C enzyme components. This patent presents therapeutic pharmaceutical formulations containing snake and/or insect venoms, or extracts from such venoms which contain, total or partial, phospholipase $A_2$ enzyme activity or $PLA_2$ epitopes. This patent presents therapeutic pharmaceutical formulations containing anti-serum to snake and/or insect venoms and/or mammalian $PLA_2$ enzymes wherein the anti-serum has been preferably affinity purified for use in treating patients suffering from neoplastic disease. This patent presents pharmaceutical formulations containing organic polymer mimic molecules generated to snake and/or insect venoms or the $PLA_2$ enzyme components thereof and/or $PLA_2$ enzymes isolated from insect, mammalian on plant cells, and/or Phospholipase C enzyme preparation or extract from such venoms which may contain, total or partial, phospholipase $A_2$ enzyme activity.

In some embodiments according to the present invention, phospholipase $A_2$ is synthetically produced or cloned.

In another aspect of the present invention, there is provided a method of treating neoplasm in a mammal in need of such treatment, comprising administering to said mammal a therapeutic agent comprising venom and/or mammalian, plant or insect anti-serum reactive with at least one Phospholipase $A_2$ enzyme.

In another aspect of the present invention, there is provided a method of treating a mammal prophylactically to prevent neoplastic development, comprising administering to said mammal a therapeutic vaccine containing venom and/or mammalian, plant or insect $PLA_2$ enzymes or part thereof as the principal antigen component.

In another aspect of the present invention, there is provided a pharmaceutical formulation containing venom and/or mammalian, plant or insect anti-serum to $PLA_2$ enzyme or part thereof in combination with anti-serum to Phospholipase C enzyme or part thereof or inhibitory compounds to Phospholipase C for use as a therapeutic agent for the therapy of a neoplastic condition in a human or animal. In some embodiments according to this aspect, the inhibitory compounds to Phospholipase C is/are one or more of EDTA, phenanthroline, chloromercuribenzoic acid, iodoacetic acid, and 1-oleoyl-2-acetyl-sn-glycerol(OAG).

In another aspect of the present invention, there is provided a pharmaceutical formulation containing one or more venoms or venom components as antigen and/or mammalian, plant or insect $PLA_2$ enzyme as antigen alone or in combination with Phospholipase C enzyme.

In another aspect of the present invention, there is provided a method of treating a mammal prophylactically to prevent neoplastic development, comprising administering to said mammal a therapeutic vaccine comprising venom and at least one adjuvant.

In this patent the affinity purified anti-serum to venoms Phospholipase $A_2$ ($PLA_2$) and mammalian or plant $PLA_2$ are shown to be active anti-proliferative neoplastic agents.

The present invention comprises the method of treating host organisms (i.e. human or animal) in need of a drug having anti-neoplastic activity comprising the administration of a therapeutically effective amount of venom anti-serum either alone or preferably in combination with a Phospholipase C inhibitor of non-toxic nature or monoclonal or polyclonal anti-serum to Phospholipase C enzyme or a vaccine containing in whole or in part venom and/or other components of animal, insect or plant origin showing Phospholipase $A_2$ and/or Phospholipase C activity. This patent presents pharmaceutical formulations containing snake and/or insect venoms, or extracts from such venoms which may contain, total or partial, Phospholipase $A_2$ enzyme activity alone or in combination with animal or plant Phospholipase $A_2$ with or without Phospholipase C inhibiting compounds or Phospholipase C mono or polyclonal anti-serum to Phospholipase C enzyme as therapeutic vaccine candidate for all neoplastic diseases. This patent presents therapeutic pharmaceutical formulations containing anti-serum to snake and/or insect venoms wherein the antiserum is preferably affinity purified for use in treating neoplastic diseases. This patent presents pharmaceutical formulations containing organic polymer mimic molecules generated to snake and/or insect and/or mammalian and/or plant $PLA_2$ enzymes or epitopes, or extract from such venoms or synthetic peptides and/or other molecules which may contain, total or partial, Phospholipase $A_2$ and C enzyme activity.

In another aspect, the present invention provides a method of inoculation of human or animal with a combination of two or more phospholipase $A_2$ enzyme types.

In some embodiments according to this aspect of the present invention, he antibody response to the inoculation confers prophylactic and/or therapeutic benefit to the patient.

In some embodiments according to this aspect of the present invention, the patient is in need of a treatment for a neoplastic condition.

In some embodiments according to this aspect of the present invention, the phospholipase $A_2$ type is Type I, Type II, Type III or Type IV.

In some embodiments according to this aspect of the present invention, the Phospholipase $A_2$ is obtained from venom.

In some embodiments according to this aspect of the present invention, the Phospholipase $A_2$ is obtained from animal or plant species.

Phospholipase $A_2$ are lipolytic enzymes that hydrolyze the sn-2-acylester bond in glycerophospholipids. Many forms of $PLA_2$ exist in nature and have been described and classified into several groups. Types I, II and III $PLA_2$ are low molecular weight peptides (13-18 kDa) extra-cellular enzymes, including pancreatic and cobra venom $PLA_2$ (type I), rattle snake and inflammatory $PLA_2$ (type II) and bee venom type III. Intracellular cytosolic $PLA_2$ belong to different groups, including the 85 kDa (type IV) and 40-75 kDa enzymes.

Affinity purified anti-serum to venoms, animal or plant tissue demonstrating the ability to bind $PLA_2$ enzymes are shown herein below, by way of example, to be active in-vitro and in-vivo anti-proliferative neoplastic agents. Accordingly, these affinity purified antisera either alone or in combination with non-toxic Phospholipase C inhibitor or anti-serum to Phospholipase C are useful in the control of proliferation of neoplastic tissue.

BACKGROUND OF THE INVENTION

There is evidence to indicate that Phospholipase $A_2$ ($PLA_2$) is involved in the pathogenesis of many diseases. Thus local and circulating levels of Phospholipase $A_2$ enzyme and enzymatic products are elevated during infection, inflammatory diseases, tissue injury and brain dysfunction and is a very early indication of neoplastic development prior to tumour cell mass being evident by conventional methods of scanning tissue tumours.

Excessive Phospholipase $A_2$ activity may promote chronic inflammation, allergic reaction, tissue damage and pathophysiological complications. These effects may be the result of accumulating Phospholipase $A_2$ products (lysophospholipids and free fatty acids, e.g. Arachidonic Acid) and destruction of key structural phospholipid membrane components, but are potentated by secondary metabolites, such as eicosanoids and platelet-activating factor. Phospholipase $A_2$ products or lipid mediators derived therefrom have been implicated in numerous activities that are an integral part of cell activation; chemotaxis, adhesion, degranulation, phagocytosis and aggregation.

Phospholipase $A_2$ secreted excessively at local sites may be responsible for tissue damage common to rheumatic disorders, alveolar epithelial injury of lung disease and reperfusion.

During acute myocardial ischemia, cytosolic Phospholipase $A_2$ and Phospholipase C activation causes increased intracellular $Ca^{2+}$. Subsequent accumulation of lysophospholipids and free fatty acids promote damage to sarcolemmal membranes leading to irreversible cell injury and eventually cell death.

Altered cytosolic Phospholipase $A_2$ and Phospholipase C activity or defects in their control and regulation is a predisposing factor to causing tumour cell development.

Prostaglandins and related eicosanoids are important mediators and regulators of both immune and inflammatory responses. Prostaglandin $E_2$ induces bone resorption and Leukotriene $B_4$ stimulates vasodilation and chemotaxis. Increased levels of Phospholipase $A_2$ is noted in Rheumatoid Arthritis (R.A.), osteoarthritis, gout, collagen and vascular diseases. Phospholipase $A_2$ induces non specific airway hyperactivity that is evident in asthma. Phospholipase $A_2$ is also elevated in peritonitis, septic shock, renal failure, pancreatis, Chrons and Graves Disease.

The activity of cell-mediated defence systems is stimulated by consecutive formation of interleukin $1\beta$(IL-$1\beta$), interleukin-2 (IL-2) and interferon $\gamma$ (IFN $\gamma$). The system is inhibited by interleukin-4 (IL-4) and also by prostaglandin $E_2$, ($PGE_2$) and histamine, which are released when the immune system is activated. The inhibition is strong in cancer patients, because $PGE_2$ is formed in many cancer cells and its formation is stimulated by IL-$1\beta$. $PGE_2$ and histamine are feedback inhibitors of cell mediated immunity.

$PGE_2$ is formed from arachidonic acid in monocytes, macrophages, cancer cells and other cells, when arachidonic acid is released from cellular phospholipids. The formation of $PGE_2$ is stimulated by several compounds, including histamine, IL-1 ($\alpha$ and $\beta$) and Tumour Necrosis Factor $\alpha$ (TNFa). $PGE_2$ inhibits the formation and receptor expression of IL-2 by increasing the level of cyclic AMP (cAMP) in helper T cells. This concomitantly decreases the formation of IFN$\gamma$.

$PGE_2$ inhibits the ability of natural killer cells (NK) to bind with tumour cells by increasing cAMP in Natural Killer Cells. This decreases tumour cell killing.

When the immune system is stimulated to destroy tumour cells, the killing is prevented because IL-$1\beta$ stimulates $PGE_2$ formation in tumour cells, which increases cAMP levels in NK cells and prevents the binding of NK and tumour cells.

The activation of the cell-mediated defence is blocked also because $PGE_2$-increases cAMP in helper T cells and inhibits the formation of IL-2 and IFN$\gamma$.

Cytotoxic T cells can also produce $PGE_2$ thus inhibiting the activity of NK cells.

A number of human and experimental animal tumours, contain and/or produce large quantities of prostaglandins (PG). Prostaglandins $E_2$ has been shown to effect significant cell proliferation in tumour growth and to suppress immune responsiveness.

Phosphatidylinositol specific phospholipase C is an important enzyme for intracellular signalling. There are at least three major classes of Phosphatidylinositol specific Phospholipase C (PtdlnsPLC: PtdlnsPLC $\beta$, $\gamma$, $\delta$). PtdlnsPLCs hydrolyse a minor membrane phospholipid, phosphatidylinositol (4, 5) bisphosphate (Ptdlns (4,5) $P_2$) to give the second messengers inositol (1, 4, 5) trisphosphate (Ins (1, 4, 5) $P_3$), which releases Ca++ from intracellular stores to increase the intracellular free CA++ concentration, and diacylglycerol which activates the Ca++ and phospholipid-dependent protein serine/threonine kinase, protein kinase C. Proteins phosphorylated by protein kinase C include transcription factors. Together, the increase in intracellular free Ca++ concentration and the activation of protein kinase C lead to a series of events that culminate in DNA synthesis and cell proliferation in tumour cells.

A number of growth factors and mitogens, including platelet-derived growth factor (PDGF), epidermal growth factor (EGF) and bombesin, act through specific receptors to increase Ptd lns PLC activity in cells. Continued stimulation of Ptd Ins PLC can lead to cell transformation.

Ptd Ins PLC activity is found to be increased in a number of human tumours. 76% of human breast cancers have detectable Ptd Ins PLC-$\gamma$ immunoreactive protein compared to only 6% in benign breast tissue.

Cytosolic Ptd lns PLC activity is increased up to >4-fold in human non-small cell lung cancer and renal cell cancer compared to normal tissue.

SUMMARY OF THE INVENTION

The present invention comprises the method of treating mammals including humans in need of a drug to prevent neoplastic tissue growth and spread by the administration of a therapeutically effective amount of venom anti-serum prepared to whole venom or to parts of the venom or components of plant or animal origin which demonstrate $PLA_2$ activity. Also enhanced anti-cancer effects both in-vitro and in-vivo have been realised by combining this affinity purified anti-serum to $PLA_2$ components and/or mammalian $PLA_2$ with a non-toxic inhibitor of Phospholipase C or with anti-serum (polyclonal or monoclonal) developed to Phospholipase C enzyme.

This patent relates to the administration of one or more compounds which can generally be described as performing their function by either directly or indirectly causing Phospholipase $A_2$ and/or Phospholipase C enzyme inhibition, wherein the said inhibition is either partial or total. In addition this patent relates to the administration of one or more compounds which can generally be described as performing their function by interaction with the neoplastic cell membrane preventing their growth or spread, thus preventing further disruption of non-involved organs of the body and causing no toxicity to the infected patient or animal being treated.

Additional aspects of the invention relates to pharmaceutical compositions containing the compounds of the invention as active ingredients, modifying unwanted immune responses, and to methods of retarding proliferation of tumour cells using the compounds and compositions of this invention.

The anti-serum to snake venom $PLA_2$ and to plant, insect, mammalian and/or to $PLA_2$ epitopes or mimic molecules are shown herein to be active anti-tumour proliferative compounds and immune enhancing. For use in this regard, the compounds of the invention are administered to mammals, including humans, in an effective amount of 0.05 to 5 gms per day per kilogram of body weight. The amount depends, of course, on the condition to be treated, the severity of the condition, the route of administration of the drug, and the nature of the subject. The drugs may be administered IV, orally, parenterally, or by other standard administration routes including targeting with liposomes/RBC.

BRIEF DESCRIPTION OF THE DRAWING FIGURES

FIG. 1 is a plot of animal weight vs. time in a toxicity study of compounds according to the present invention.

FIG. 2 is a plot of relative tumor volume vs days in a test of the effect anti-serum to snake venom on tumour growth retardation.

FIG. 3A is a plot of MTT uptake vs. dilution of antiserum in an in vitro screening of an affinity purified anti-serum to snake venom preparation against human colorectal tumour C170HM2 tumour cell line.

FIG. 3B is a plot of MTT uptake vs. dilution of antiserum in an in vitro screening of an affinity purified anti-serum to snake venom preparation against human bladder tumour T24 tumour cell line.

FIG. 3C is a plot of MTT uptake vs. dilution of antiserum in an in vitro screening of an affinity purified anti-serum to snake venom preparation against human lymphoma tumour MOLT 4 tumour cell line.

FIG. 3D is a plot of MTT uptake vs. dilution of antiserum in an in vitro screening of an affinity purified anti-serum to snake venom preparation against human pancreatic tumour PAH 1 tumour cell line.

FIG. 3E is a plot of MTT uptake vs. dilution of antiserum in an in vitro screening of an affinity purified anti-serum to snake venom preparation against human breast tumour MDA 468 tumour cell line.

FIG. 1F is a plot of MIT uptake vs. dilution of antiserum in an in vitro screening of an affinity purified anti-serum to snake venom preparation against human small cell lung tumour 841 tumour cell line.

FIG. 3G is a plot of MTT uptake vs. dilution of antiserum in an in vitro screening of an affinity purified anti-serum to snake venom preparation against human gastric ST24 tumour cell line.

FIG. 3H is a plot of MTT uptake vs. dilution of antiserum in an in vitro screening of an affinity purified anti-serum to snake venom preparation against human ovarian OVCAR3 tumour cell line.

FIG. 4 is a plot of mean tumour cross-sectional area vs. time in an experiment testing the effect of affinity purified anti-serum to snake venom on the mean cross-sectional area of C170HM2 in nude mice.

FIG. 5 is a plot of tumour weights in the experiment testing the effect of affinity purified anti-serum to snake venom on the mean cross-sectional area of C170HM2 in nude mice.

FIG. 6A is a plot of MTT uptake vs. dilution of antiserum in an in vitro screening of an affinity purified anti-serum to snake venom preparation in combination with a phospholipase C inhibitor 1-oleoyl-2-acetyl-sn-glycerol (OAG) against human breast tumour MDA 468 tumour cell line.

FIG. 6B is a plot of MTT uptake vs. dilution of antiserum in an in vitro screening of an affinity purified anti-serum to snake venom preparation in combination with a phospholipase C inhibitor 1-oleoyl-2-acetyl-sn-glycerol (OAG) against human small cell lung tumour 841 tumour cell line.

FIG. 6C is a plot of MTT uptake vs. dilution of antiserum in an in vitro screening of an affinity purified anti-serum to snake venom preparation in combination with a phospholipase C inhibitor 1-oleoyl-2-acetyl-sn-glycerol (OAG) against human renal TK-10 tumour cell line.

FIG. 7 is a plot of tumour cross-sectional area vs. time in an experiment testing the effect of affinity purified anti-serum to snake venom in combination with the Phospholipase C inhibitor (OAG) on the mean cross-sectional area of MDA 468 in Scid mice.

DETAILED DESCRIPTION OF THE INVENTION

The therapeutic activity of the compounds of this invention are demonstrated by inhibition of the tumour cell lines in-vitro and in-vivo. The compounds were tested for toxicity in Scid mice. Results as in FIG. 1 [toxicity data].

Toxicity Study

Method

Female Scid mice (6-8 weeks of age) were treated with either a Neat or a 1:10 dilution of the anti-serum preparation, subcutaneously (0.1 ml, daily) for a period of 14 days. The weights of the mice were measured daily. At termination, organs were removed and fixed in formalin for histological examination.

Results

No toxicity, as assessed by animal weights and clinical well-being, was evident (FIG. 1).

The compounds of this invention may be combined with other known anti-inflammatory/immunosuppressive or chemotherapeutic agents such as steroids or non-steroidal anti-inflammatory agents in the pharmaceutical compositions and methods described herein.

Anti-serum to snake and/or insect venoms and/or mammalian and/or PLA$_2$ enzyme or its epitopes can be used as a therapeutic treatment in diseases where elevated levels of Phospholipase A$_2$ are evident, (e.g. Rheumatoid Arthritis, see Table B). It is also envisaged that this novel therapy with anti-serum to venom PLA$_2$ (snake or insect) and/or to PLA$_2$ components (derived from animal or plant) can be applied as a prophylactic therapy by using sub-lethal doses of venoms or the venom PLA$_2$ enzyme extracts together with mammalian or plant PLA$_2$ or synthetic peptides demonstrating PLA$_2$ activity plus adjuvant to stimulate an immunoglobulin response within the patient, see results—Vaccine Efficacy in Balb/c mice. It is also envisaged that a synthetic peptide incorporating the Phospholipase A$_2$ and/or Phospholipase C activity could be used to generate said anti-serum or therapeutic agent or vaccine. Use may also be made in the generating of this therapeutic vaccine/anti-serum by using the known sequence homology that exists between human Phospholipase A$_2$ and snake/insect venoms together with animal PLA$_2$ used in combination with compounds known to inhibit Phospholipase C activity or anti-serum developed to this enzyme.

Sustained or directed release compositions can be formulated, e.g. liposomes or those wherein the active compound is protected with differentially degradable coatings, e.g. by microencapsulation, multiple coatings, etc. It is also possible to freeze-dry the new compounds and use the lyophilizates obtained, for example, for the preparation of products for storage and subsequent injection.

Experimentation

The compounds of this invention can be identified as antiserum to snake or insect venoms mammalian or plant PLA$_2$ or parts thereof or Phospholipase C or mimic molecules generated to venoms or mammalian PLA$_2$ molecules and/or Phospholipase C or parts thereof also the pharmaceutical use of venoms or parts thereof and/or mammalian PLA$_2$ or enzyme components as vaccine antigen are incorporated. Non-toxic compounds showing anti-phospholipase C activity can be incorporated with the anti-serum to PLA$_2$ of any origin, or mimic molecules demonstrating Phospholipase A$_2$ activity.

In certain applications of this therapy it may be necessary to curtail the ADCC reaction which could cause scrum sickness and to ensure that this does not occur the IgG (FC) component is enzymatically cleaved from the affinity purified immunoglobulin so that natural killer cells will not react to the immunoglobulin in the anti-serum.

Ability of Anti-Serum to Snake Venom to Inhibit Phospholipase A$_2$ Enzyme Isolated from Human Synovial Fluid (Table A2).

The inhibition of Phospholipase A$_2$ enzyme from synovial fluid isolated from a patient with Rheumatoid Arthritis was tested with a range of dilutions of anti-serum to snake venom. Anti-serum to snake venom generated in horse, reconstituted in 10 ml sterile water. The following dilutions were used 1:10, 1:20, 1:40 and 1:60. The method used was as outlined in "Infection and Immunity, September 1992, p. 3928-3931. Induction of Circulating Group II Phospholipase A$_2$ Expression in Adults with Malaria.

TABLE A2

Results

| Dilution | Inhibition |
| --- | --- |
| 1:10 | 63% |
| 1:20 | 50% |

TABLE A2-continued

Results

| Dilution | Inhibition |
| --- | --- |
| 1:40 | 35% |
| 1:60 | 29% |

In-Vitro Testing of Un-Affinity Purified Snake Venom.

A range of tumour cell lines were tested with 3 concentrations of the anti-serum to snake venom by the MTT Assay. This anti-serum was not affinity purified. MTT Assay described by Alley et al, (Cancer Research, 48: 589-601, 1988) See Table B.

TABLE B

SUMMARY OF RESULTS

| Dilution | % of Control |
| --- | --- |
| Molt 4: Human T cell Lymphoma Cancer | |
| Serum-containing | |
| Neat | 48.1 |
| 1:10 | 53.7 |
| 1:20 | 40.8 |
| Serum-Free | |
| Neat | 58.7 |
| 1:10 | 51.2 |
| 1:20 | 40.6 |
| MDA 468: Human Breast Cancer | |
| Serum-containing | |
| Neat | 8.0 |
| 1:10 | 53.7 |
| 1:20 | 58.9 |
| Serum-Free | |
| Neat | 15.4 |
| 1:10 | 48.4 |
| 1:20 | 58.9 |
| C17OHM2: Human Colon Cancer | |
| Serum-containing | |
| Neat | 9.3 |
| 1:10 | 61.4 |
| 1:20 | 55.6 |
| Serum-Free | |
| Neat | 15.2 |
| 1:10 | 47.3 |
| 1:20 | 49.5 |
| Pan 1: Human Pancreatic Cancer | |
| Serum-Containing | |
| Neat | 9.3 |
| 1:10 | 47.5 |
| 1:20 | 49.2 |
| Serum-Free | |
| Neat | 43.1 |
| 1:10 | 53.2 |
| 1:20 | 69.4 |
| 841: Human small cell lung cancer | |
| Serum-containing | |
| Neat | 25.2 |
| 1:10 | 45.5 |
| 1:20 | 51.1 |
| Serum-Free | |
| Neat | 63.4 |
| 1:10 | 60.1 |
| 1:20 | 59.8 |

TABLE B-continued

SUMMARY OF RESULTS

| Dilution | % of Control |
|---|---|
| T24: Human Bladder Cancer Serum-containing | |
| Neat | 68.5 |
| 1:10 | 75.1 |
| 1:20 | 76.2 |
| Serum-Free | |
| Neat | 84.1 |
| 1:10 | 87.9 |
| 1:20 | 88.4 |

Testing Un-Affinity Purified Anti-Serum to Snake Venom Against B16F1 Melanoma Cell Line.
Mice
C57BL/6
Procedure The mice were inoculated with $0.5 \times 10^6$ B16 F1 melanoma cells subcutaneously (sc) into flank region. Once palpable tumours had developed the mice received daily sc injections as follows: —

| | number of mice |
|---|---|
| A - Sterile water 100 µl | 6 |
| B - anti-serum (full strength) 100 µl | 6 |
| C - anti-serum (diluted 1:10) 100 µl | 6 |

Figure 2:
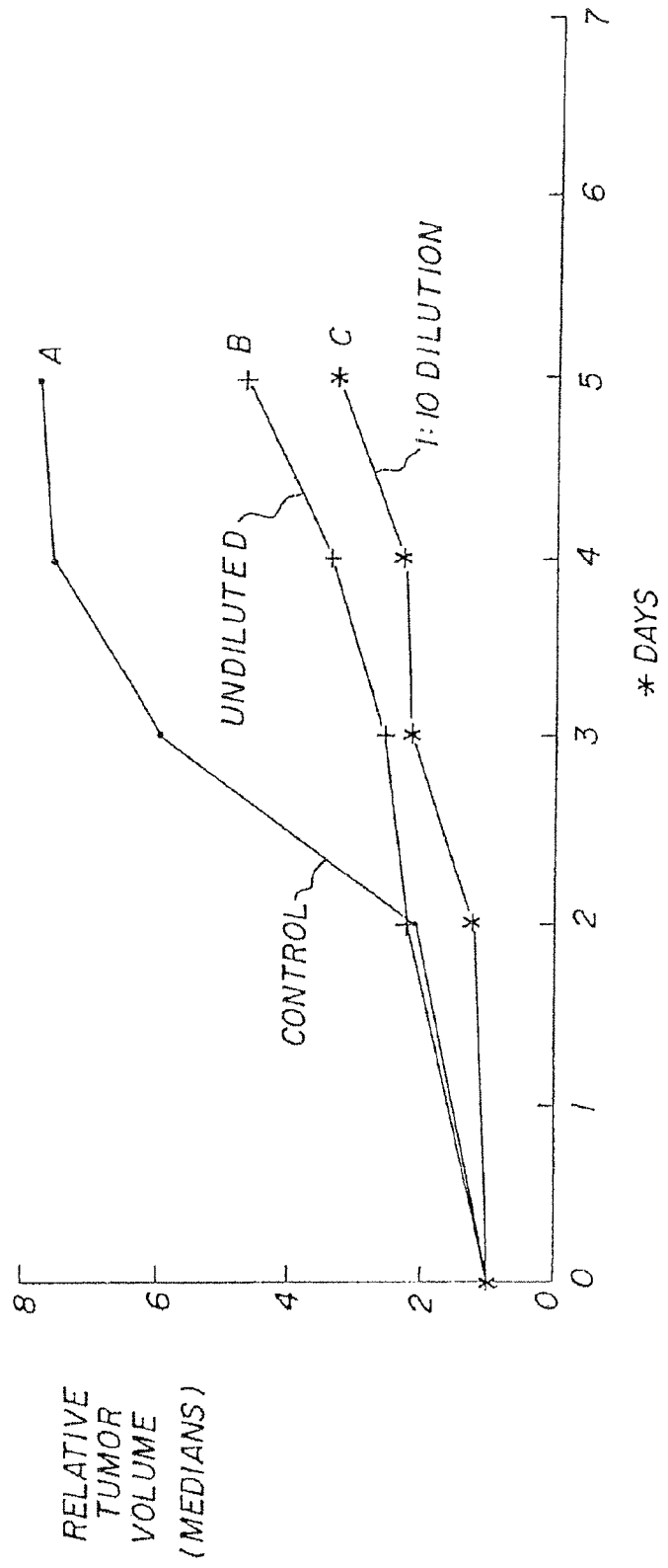

The dimensions of the tumours were taken daily using callipers. Once the tumours of the control mice were approximately 1.5 cm or larger in diameter all mice were killed. The tumours were removed and weighed.
Results Small tumours were first discernible by palpitation in all mice 6-7 days after inoculation. The changes in volume as measured by callipers, together with tumour weights at autopsy. See FIG. 2 [Effect of un-affinity purified anti-serum to snake venom on Melanoma B161F1 Growth] for effect of anti-serum to snake venom on tumour growth retardation.

Figures 3A, 3B:
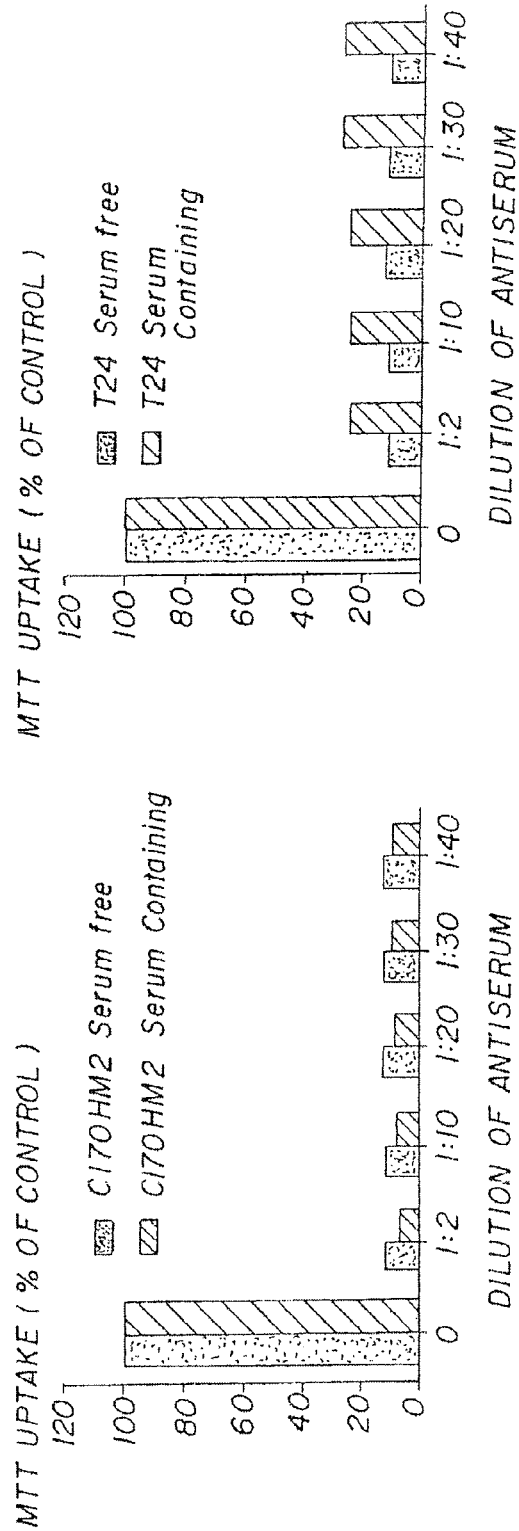
Figures 3E, 3F:
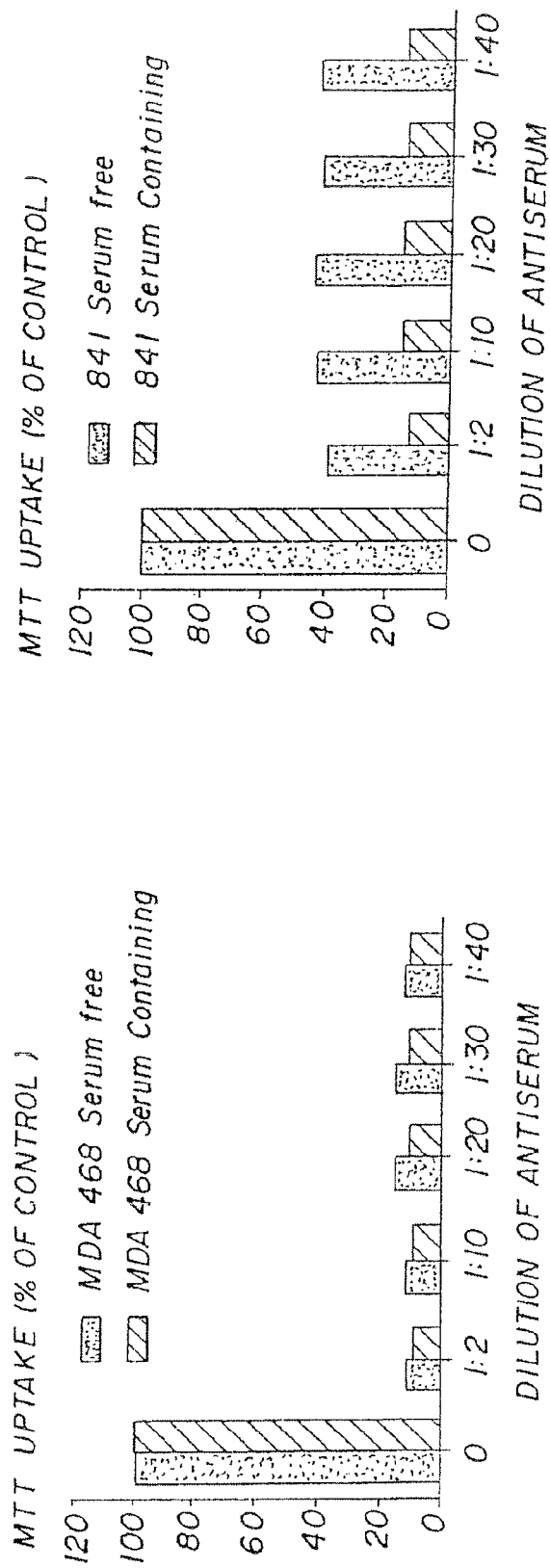
Figure 3H:
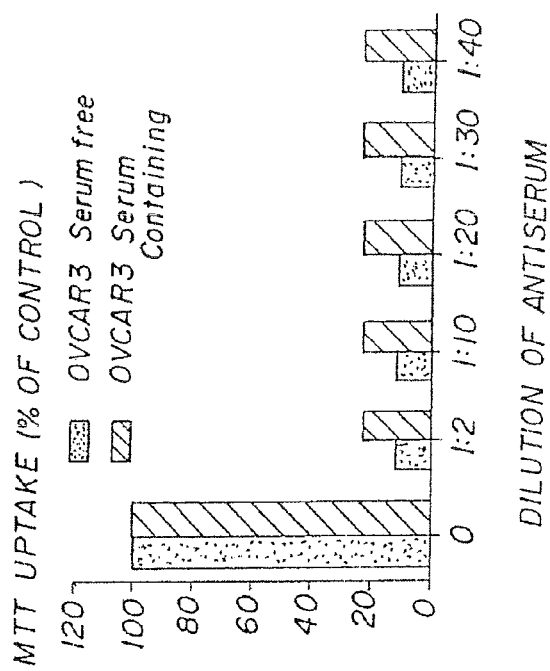
Figure 3G:
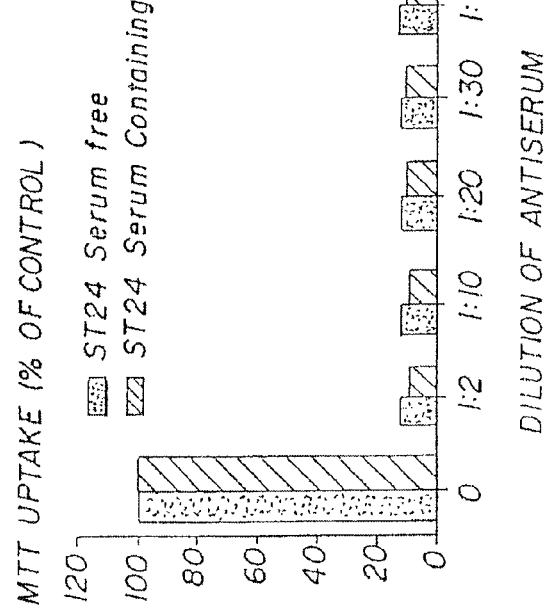

In-Vitro Screening of the Affinity Purified Anti-Serum to Snake Venom Preparation Against a Range of Tumour Cell Lines (Illustrated in FIG. 3A [Human colorectal tumour C170HM2], FIG. 3B [Human bladder tumour T24], FIG. 3C [Human lymphoma tumour MOLT 4], FIG. 3D [Human pancreatic tumour PAN 1], FIG. 3E [Human breast tumour MDA 468], FIG. 3F [Human Small Cell Lung Tumour 841], FIG. 3G [Human gastric ST24], and FIG. 3H [Human Ovarian OVCAR3])
Introduction The in-vitro inhibitory effects of the horse generated anti-serum to snake venom preparation, previously evaluated were obscured due to serum enhancement of tumour cell growth. Thus in the following assay, affinity purified anti-serum to snake venom was evaluated.
Method The cell lines were seeded into 96 well plates at a cell concentration of $10^4$ cells per well in both serum free (Hams F12:RPMI 1640+0.5% bovine serum albumen) and serum-containing medium (RPMI 1640+10% heat inactivated foetal calf serum). The anti-serum preparation was diluted in the corresponding medium and added to the wells, 2-3 hours after the cells (to allow for cell adherence). The plates were incubated at 37° C. in ~5% $CO_2$ for 3 days. The cells were then incubated with 1 mg/ml MTT (methyl thiazol tetrazolium) for 4 hours at 37° C. The crystals were then solublised with dimethyl sulphoxide and the absorbance measured at 550 nm.
Results The test anti-sera inhibited all of the cell lines at all concentrations examined. The level of inhibition was statistically significant from the untreated control at all anti-serum dilutions, with all cell lines as assessed by a one way analysis of variance.

In-Vivo Test

The effects of affinity purified anti-serum to snake venom on human colorectal $C17OHM_2$ cell line.
Materials and Methods C170 $MH^2$ cells were injected subcutaneously into the left flank of ten male nude mice. The mice were allocated randomly to two groups.

Figure 4:
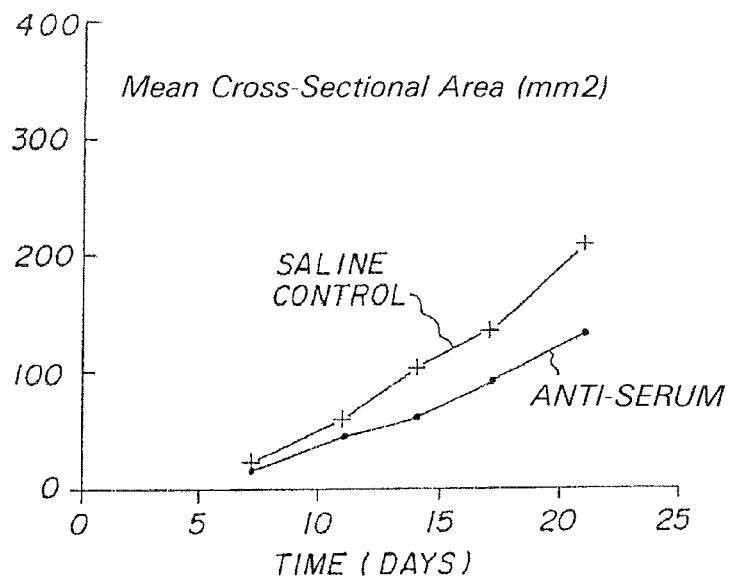

Group 1—100 µl anti-serum twice daily intravenously (IV)
Group 2—100 µl PBS twice daily IV Tumours were measured twice weekly, using callipers, in two dimensions. Cross-sectional areas were calculated. The mice were also weighed once weekly. The therapy was terminated at day 22.
Results The cross-sectional areas were measured at increasing time points during the experiment, as shown in FIG. 4 [Effect of affinity purified anti-serum to snake venom on the mean cross-sectional area of C170HM2 in nude mice]. The affinity purified anti-serum preparation induced a slowing in growth when compared to saline controls. An ANOVA was performed on the results in which the treatment was evaluated with respect to time, and shows a significance of P=0.028.

Figure 5:
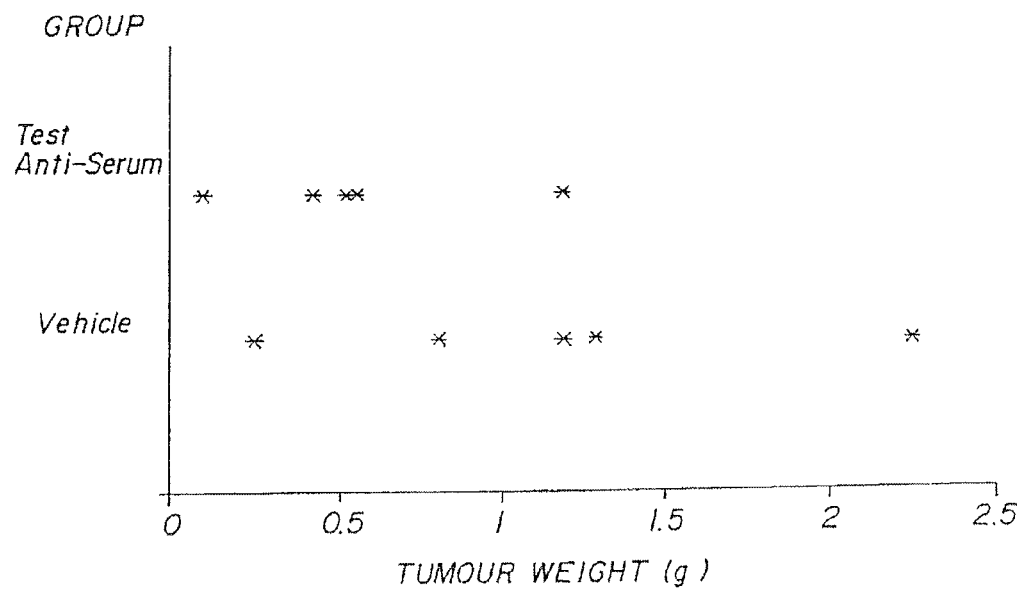

At the termination of the experiment, the tumours were weighed and the results are shown in FIG. 5 [Effect of affinity purified anti-serum to snake venom on the final tumour weight of C170HM2]. No toxic effect of the affinity purified anti-serum preparation was observed.

Figure 6A:
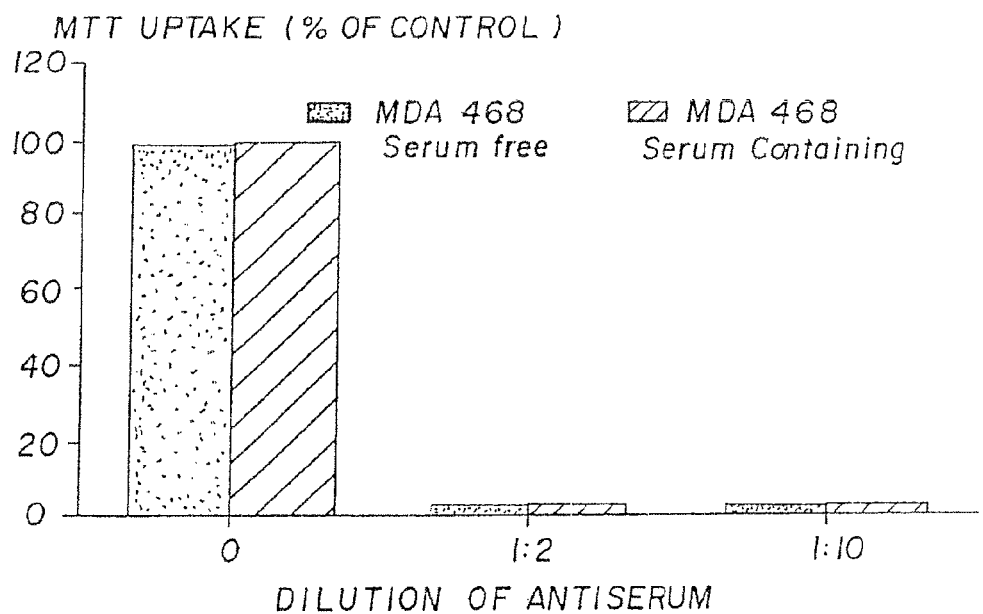
Figure 6B:
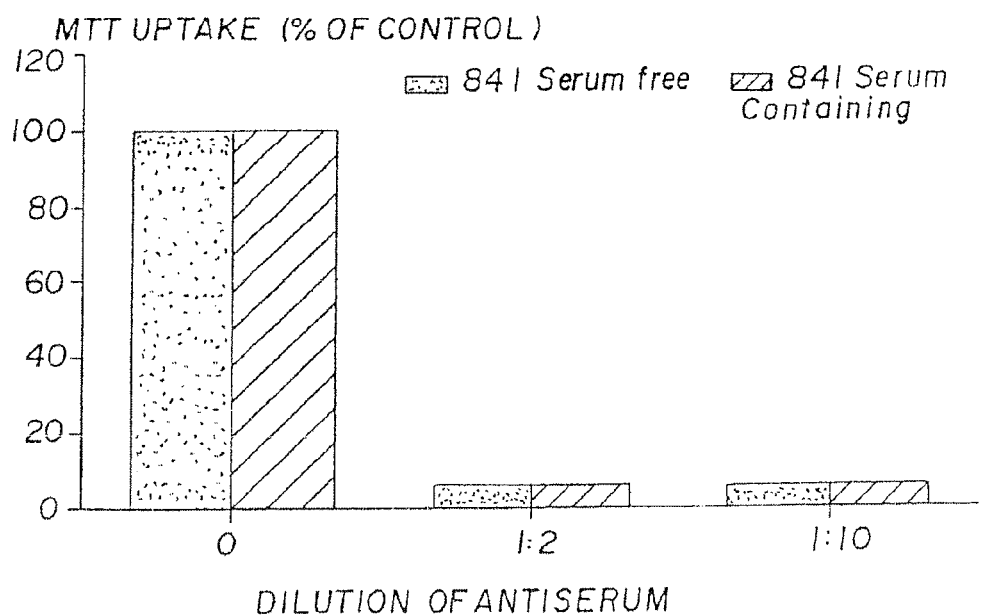
Figure 6C:
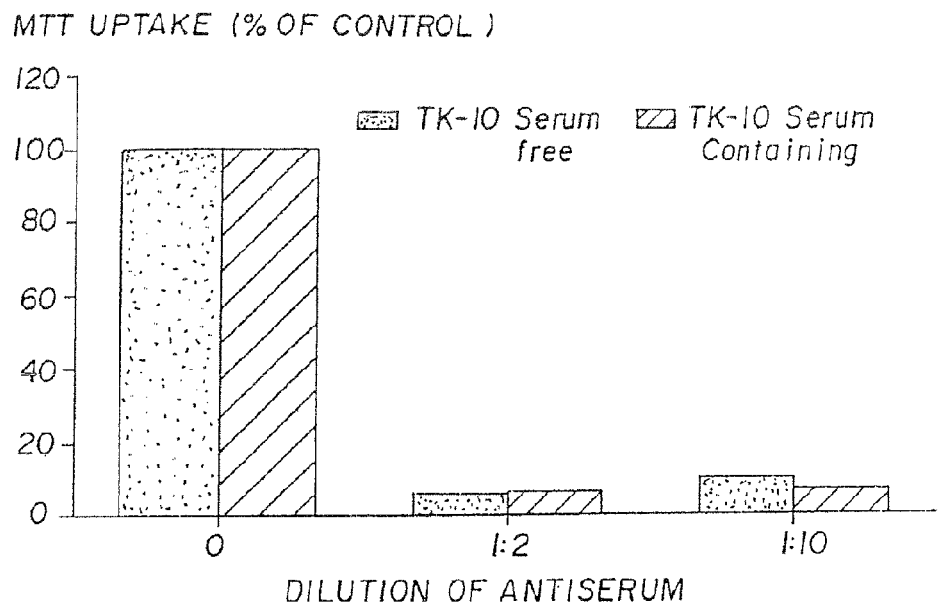

In-Vitro Screen of the Affinity Purified Anti-Serum to Snake Venom Preparation in Combination with a Phospholipase C Inhibitor 1-oleoyl-2-acetyl-sn-glycerol (OAG) 5µ Molar, on a Range of Cancer Cell Lines.
Methods The affinity purified anti-serum to snake venom preparation was diluted 1:2 and 1:10 and was combined with 5µ molar OAG and added to the wells as previously described for the MTT Assay. The cell lines tested were Human Breast tumour, MDA 468, Human small cell lung tumour 841 and Human renal TK-10. Results as shown in FIG. 6A [Affinity purified anti-serum to snake venom and (OAG) a Phospholipase C inhibitor combination—Human breast tumour MDA 468], FIG. 6B [Affinity purified anti-serum to snake venom and (OAG) a phospholipase C inhibitor combination—Human small cell lung tumour 841] and 6C [Affinity purified anti-serum to snake venom and (OAG) a phospholipase C inhibitor combination—Human renal TK-10].

Figure 7:
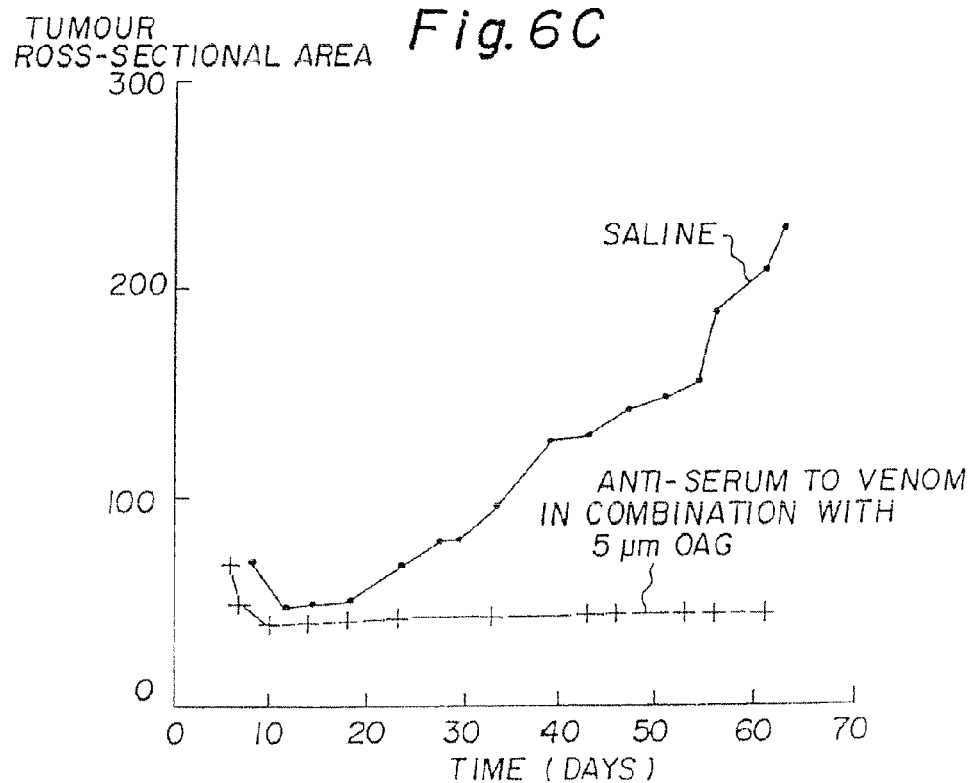

In-Vivo Testing of the Combination of Affinity Purified Anti-Serum to Snake Venom and 1-oleoyl-2-acetyl-sn-glycerol (OAG) at 5 µm Concentration on the Growth of MDA 468 Cell Line.
Method MDA 468 tumours were aseptically removed from donor female Scid mice. The tissue was aseptically minced, pooled and implanted into anaesthetised female Scid mice (anaesthetic comprised of a 0.2 ml injection of Hypnorm (Jannsen): Hyonovel (Roche): distilled water in a 1:1:5 ratio). Tissue implants consisted of 3-5 $mm^2$ pieces and after subcutaneous transplantation into the left flank, the incision was clipped. The Scid mice were then randomised into 2 groups of 10 animals. They were treated daily with a 0.2 ml subcutaneous injection (in the opposite flank to the tumour graft) of a combination of affinity purified anti-serum to snake venom and 5 μm molar of (OAG) dilution of the anti-serum preparation. The control animals received 0.2 ml phosphate buffered saline, pH 7.6. All animals were terminated on day 63, and the tumours were dissected out, weighed and processed for histology. Results are in FIG. 7 [Effect of the affinity purified anti-serum to venom in combination with the Phospholipase C inhibitor (OAG) 5 μm].

Vaccine Efficacy in Balb/c mice after challenge with WEHI-3 cell.

The objective of study is to demonstrate the efficacy of sub-lethal levels of Russelli vipera venom entrapped in liposomes and porcine phospholipase $A_2$ enzyme entrapped in liposomes working in combination to confer a sustained and protective antibody response to a challenge by Leukaemia cells (WEHI-3 cells)

The Russelli vipera venom was toxoided with 2% osmium tetroxide and entrapped in liposomes (egg phosphocholine and cholesterol). The liposomes were sterilised.

The Porcine Phospholipase $A_2$ enzyme was entrapped in liposomes (egg phosphocholine, and cholesterol) and were sterilised.

Immunisation of mice consisted of an initial subcutaneous injection of 0.25 mls (containing 250 μg of venom) and 3 days later the mice were injected subcutaneously with 0.25 mls of porcine $PLA_2$ (containing 250 μg of porcine $PLA_2$. Boosters of each vaccine were given at 3 week intervals.

Control mice were injected with 0.25 mls of sterile physiological saline on days corresponding to test mice inoculations.

Animals

Balb/c mice (20-25 g) were used in the study. 15 mice were used in each group.

Group I—test mice

Group II—control mice

Challenge

The immunised mice and controls were challenged by intravenous injection into tail vein with approximately $5 \times 10^5$ leukemic cells (WEHI-3 cells) on day 30 of study.

Test mice are observed for extended life span after the death of the control mice after approximately 24 days.

Results Obtained

All control mice died of leukaemia within the allotted time span of 24 days. The venoid combination inoculation protected the vaccinated group from the cancer cell challenge and there was a 100% survival rate at day 35 when the experiment was terminated.

Without further elaboration, it is believed that one skilled in the art can, using the preceding description, utilise the present invention to its fullest extent. The preferred specific embodiments are, therefore, to be construed as merely illustrative, and not limitative of the disclosure in any way whatsoever.

What is claimed is:

1. A method of treating neoplasm in a mammal in need of such treatment, comprising administering to said mammal a therapeutic agent comprising mammalian, plant or insect anti-serum to venom.

2. A method according to claim 1 wherein the anti-serum is either polyclonal or monoclonal.

3. A method of treating a mammal to prophylactically attenuate neoplastic development, comprising administering to said mammal a therapeutic vaccine comprising venom.

4. A pharmaceutical formulation comprising snake venom and at least one material selected from the group consisting of anti-serum to phospholipase C and phospholipase C enzyme inhibitor.

5. A method according to claim 3, wherein the administration is part of a combination therapy with at least one other therapeutically effective agent.

6. A method according to claim 3 wherein the administration is in combination with at least one adjuvant.

7. A pharmaceutical formulation comprising mammalian, plant or insect anti-serum to venom and anti-serum to Phospholipase C enzyme or inhibitory compounds to Phospholipase C.

8. A pharmaceutical formulation according to claim 7, wherein the anti-serum to venom is produced synthetically by molecular imprinting of template organic molecules.

9. A pharmaceutical formulation according to claim 7, wherein the anti-serum is generated either in a monoclonal and/or polyclonal form.

10. A pharmaceutical formulation according to claim 7, wherein the anti-serum is generated in eggs, producing antibodies which do not react with the human Compliment system.

11. A pharmaceutical formulation according to claim 7, wherein the anti-serum is generated in mammals and extracted from the colostrum.

12. A pharmaceutical formulation according to claim 7 wherein the anti-serum to venom and/or the anti-serum to phospholipase C enzyme are produced synthetically by molecular imprinting of template organic molecules using these enzymes.

13. A pharmaceutical formulation according to claim 7, wherein the anti-serum is generated in mammals and extracted from the colostrum and affinity purified for use in oral administration to patients either alone or in combination with anti-serum similarly produced to human Phospholipase C enzyme components.

14. A pharmaceutical formulation comprising mammalian, plant or insect anti-serum to venom and at least one other therapeutically effective agent.

15. A pharmaceutical formulation comprising snake venom and at least one adjuvant.

16. A method of treating neoplasm in a mammal in need of such treatment, comprising administering to said mammal a therapeutic agent comprising venom.

* * * * *

UNITED STATES PATENT AND TRADEMARK OFFICE
CERTIFICATE OF CORRECTION

PATENT NO. : 8,580,744 B2  
APPLICATION NO. : 13/444416  
DATED : November 12, 2013  
INVENTOR(S) : Shanahan-Prendergast Page 1 of 1

It is certified that error appears in the above-identified patent and that said Letters Patent is hereby corrected as shown below:

In the Specification

Column 1, Lines 22-23 CROSS-REFERENCE TO RELATED APPLICATIONS

Please change: "PCT/1B97/01091" to -- PCT/IB97/01091 --

Signed and Sealed this  
Fourth Day of February, 2014

Michelle K. Lee  
*Deputy Director of the United States Patent and Trademark Office*